United States Patent [19]

van der Jagt

[11] Patent Number: Plant 6,481

[45] Date of Patent: Dec. 20, 1988

[54] CHRYSANTHEMUM NAMED REGARD

[75] Inventor: Martinus van der Jagt, Ter Aar, Netherlands

[73] Assignee: Chrysanthemum Breeders Association, N.V., Curacao, Netherlands Antilles

[21] Appl. No.: 3,601

[22] Filed: Jan. 15, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

A new and distinct cultivar of Chrysanthemum plant named Regard, bearing large sized orange blossoms with a orange center and a performance of sixteen days.

3 Drawing Sheets

BACKGROUND OF THE NEW PLANT

The new plant of the present invention relates to the Chrysanthemum genus.

ORIGIN AND HISTORY OF THE PLANT

The new plant according to the present invention comprises a new and distinct cultivar of chrysanthemum plant which is a crossbreed of unknown parents. The new cultivar was discovered by Martinus van der Jagt at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a large sized bloom and orange color.

BRIEF DESCRIPTION OF THE DRAWINGS

The present new and distinct chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage of the new cultivar.

DESCRIPTION OF THE NEW PLANT

This new variety of Chrysanthemum is of the botanical classification *Chrysanthemum morifolium,* named Regard. When grown in the vicinity of Ter Aar, Holland, it has a response time of approximately eight and one half weeks. This new variety produces large sized orange blooms with an orange center having a performance of sixteen days. This new variety of Chrysanthemum has been found to retain its distinctive characteristics throughout successive propagations and may be planted under conventional greenhouse conditions in Holland between weeks 1 to 52.

The following is a description of the plant and characteristics that distinguish it over related known varieties and its antecedents:

Botanical classification: *Chrysanthemum morifolium.*

Bud:

*Size.*—Large (cross section: 1.6 cm, height: 1.4 cm).

*Form.*—Round and of a high form.

*Outside color.*—Greyed orange 167A.

Bloom:

*Size.*—Large.

*Fully expanded.*—9 cm.

*Borne.*—Single and several.

*Stems.*—Strong and thick.

*Forms.*—Anemone type.

*Permanence.*—16 days (at 18°-20° C.).

Color:

*Center of flower (disk floret).*—The cushion: greyed orange 167A; The green spot; green 134A.

*Base of petals.*—Greyed orange 167B.

*Inside of petals.*—Greyed orange 163A.

*Reverse of petals.*—Greyed orange 163D.

*Outer petals.*—Greyed orange 163B.

*Tonality from a distance.*—An orange anemone-type flower with a compact "cushion", a high number of petals.

*Discoloration.*—May discolor to greyed orange 163C at maturity.

Petals:

*Texture.*—Upperside: smooth. Underside: rough.

*Number.*—30-33.

*Cross-section.*—Flat, no keels.

*Arrangement.*—Imbricated.

*Persistence.*—Good. Petals are all the time untidy but do not reflex more.

*Fragrance.*—Typical Chrysanthemum.

Reproductive organs:

*Stamens.*—In the cushion petals, length: 4 mm.

*Pollen.*—Some, but it does not appear.

*Styles.*—Thin, green, length: 4 mm.

*Stigmas.*—Small, width approx: 0.3 mm.

*Ovaries.*—Enclosed in calyx.

Plant:

*Form.*—Spray mum meant for erect culture.

*Growth.*—Vigorous.

*Height.*—105 cm.

*Peduncle.*—Near the top: 14 cm. Near the middle: 22 cm. Near the bottom: 27 cm.

*Internodes.*—2-3 cm.

*Flowering response.*—8½ weeks.

Foliage:

*Color.*—Upperside: yellow green 147A. Underside: yellow green 148B.

*Size.*—Length: 12 cm. Width: 8 cm (large).

*Quantity.*—35-38.

*Shape.*—Pointed, deeply undulated.

*Texture.*—Upperside: Rough. Underside: Smooth, very hirsute.

*Ribs and veins.*—Ribs and veins not so well developed. Upperside: Ribs and veins well. Underside: defined at both sides.

*Edge.*—Undulated.

In the description above, color references are made to the "R.H.S. Colour Chart" issued by The Royal Horticultural Society, in association with the Flower Council of Holland, Edition February 1986.

What is claimed:

1. A new and distinct cultivar of Chrysanthemum named Regard, as described and illustrated in the foregoing specification and accompanying drawings.

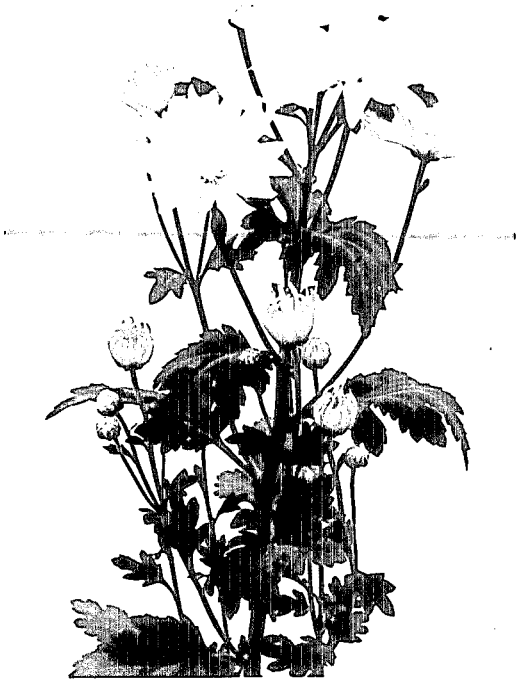

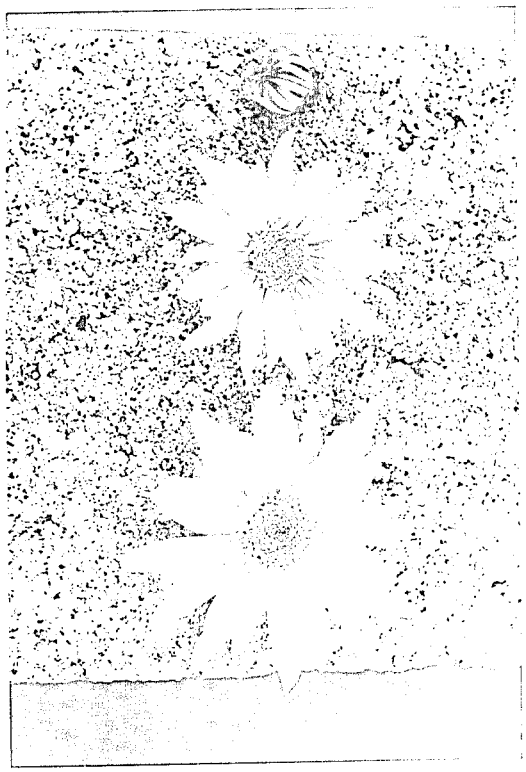

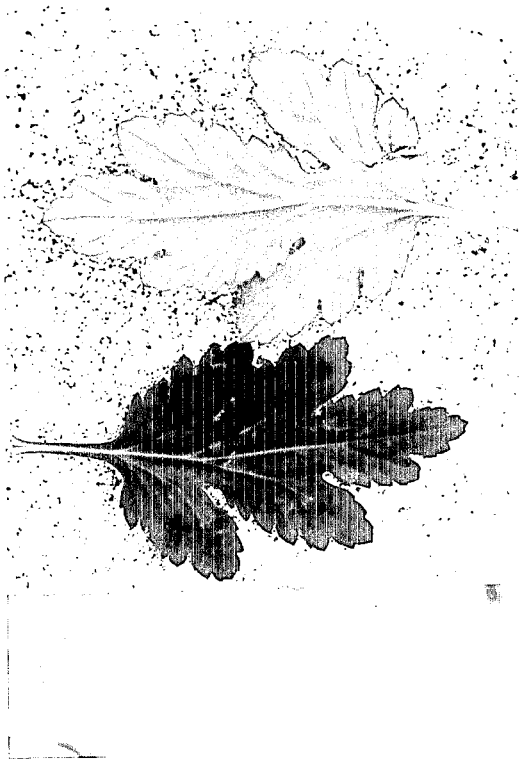

* * * * *